United States Patent [19]
Toriu et al.

[11] Patent Number: 5,183,041
[45] Date of Patent: Feb. 2, 1993

[54] TRANSCUTANEOUS ELECTRIC NERVE STIMULATOR

[75] Inventors: Mamoru Toriu, Sayama; Mitsuru Kitamura, Yokohama, both of Japan

[73] Assignees: Omron Tateisi Electronics Co., Kyoto; ITO Co., Ltd., Tokyo, both of Japan

[21] Appl. No.: 389,583

[22] Filed: Aug. 4, 1989

[30] Foreign Application Priority Data

Aug. 11, 1988 [JP] Japan .......................... 63-106499[U]

[51] Int. Cl.⁵ ............................................. A61N 1/08
[52] U.S. Cl. .................................................. 128/421
[58] Field of Search .................... 128/421, 422, 419 R

[56] References Cited

U.S. PATENT DOCUMENTS

| | | | |
|---|---|---|---|
| 4,112,923 | 9/1978 | Tomecek | 128/419 R |
| 4,580,570 | 4/1986 | Sarrell et al. | 128/423 R |
| 4,644,955 | 2/1987 | Mioduski | 128/422 |
| 4,688,574 | 8/1987 | Dufresne | 128/421 |
| 4,759,368 | 7/1988 | Spanton et al. | 128/421 |

FOREIGN PATENT DOCUMENTS

| | | |
|---|---|---|
| 3500118 | 7/1986 | Fed. Rep. of Germany . |
| 3734036 | 2/1988 | Fed. Rep. of Germany . |
| 2052991 | 7/1979 | United Kingdom . |
| 2052994 | 2/1980 | United Kingdom . |

OTHER PUBLICATIONS

Mettler Electronics Corp., Jun., 1986.
Mettler Electronics Corp., "The Sys*Stim 207", Jun., 1986.
Empi, "Hands on Therepy They Can Take Home," 1987.

*Primary Examiner*—Kyle L. Howell
*Assistant Examiner*—Kennedy J. Schaetzle
*Attorney, Agent, or Firm*—Fish & Richardson

[57] ABSTRACT

A transcutaneous electric nerve stimulator having a plurality of treatment modes and producing a low-frequency pulse of a frequency corresponding to a selected treatment mode is provided with a plurality of indicators in association with the respective treatment modes such that one of the indicators corresponding to the selected treatment mode is caused to blink in synchronism with the produced low-frequency pulse.

3 Claims, 2 Drawing Sheets

TRANSCUTANEOUS ELECTRIC NERVE STIMULATOR

BACKGROUND OF THE INVENTION

1. Field of the Invention

The present invention relates to a transcutaneous electric nerve stimulator in which low-frequency signals are applied via electrodes to a human body so as to conduct a treatment for stiffness paralysis, a pain, and the like of the human body.

2. Description of the Prior Art

Conventionally, there has been conducted a treatment in which a transcutaneous electric nerve stimulator is used to apply low-frequency pulses onto a human body so as to ease stiffness, paralysis, pain, and the like of the body.

FIG. 3 is a functional block diagram showing the electric configuration of a conventional transcutaneous electric nerve stimulator.

In FIG. 3, the system includes a pulse generator 1 to generate low-frequency pulses, namely, to produce pulses having a frequency corresponding to a treatment mode selected by use of treatment selection switches SWa, SWb, or SWc. For example, when the treatment selection switch SWa, SWb, or SWc is turned on, there are produced pulses of 1 Hz, 10 Hz, and 50 Hz, respectively. Furthermore, the pulse generator 1 is provided with light emitting diodes Ra to Rc, which indicate the utilization states of the treatment modes associated respectively with the treatment selection switches SWa, SWb, and SWc. For example, in the case where treatment selection switch SWa, SWb, or SWc is turned on, the light emitting diode Ra, Rb, or Rc is turned on respectively. Moreover, in the pulse generator 1, there is arranged a light emitting diode Rd for monitoring whether or not pulses are being outputted so as to blink each time a pulse is generated. The pulse generator 1 delivers the pulse to an output circuit 2, which is employed to amplify the pulse supplied from the pulse generator 1 to a predetermined level such that the resultant pulse is sent to an output adjuster 3. The output adjuster 3 in turn achieves an adjustment of a level (peak value) of the pulse supplied from the output circuit 2. The adjustment is carried out, for example, in response to an operation in which the operator rotates a control switch. The output adjuster 3 delivers the obtained pulse via a terminal $T_0$ to electrodes, not shown, such that the pulse is applied therefrom onto a human body.

Incidentally, in the transcutaneous electric nerve stimulator of the prior art, since the light emitting diodes Ra to Rc are disposed to respectively indicate the utilization states of the respective treatment mode selection switches SWa to SWc and the light emitting diode Rd is arranged to monitor the output state of the pulses, the display operation is complicated. In addition, even with such complexity, consideration has not been given to reduction of the number of these light emission diodes so as to minimize the production cost of the stimulator.

SUMMARY OF THE INVENTION

It is therefore an object thereof of the present invention to provide a transcutaneous electric nerve stimulator, which has been devised under the conditions above, capable of reducing the number of the light emitting diodes so as to reduce the complexity (to effect simplification) and to minimize the cost of the system.

In accordance with the invention, in order to achieve the object above, a transcutaneous electric nerve stimulator having indicators each for indicating a treatment mode disposed for each treatment mode and chosen by use of treatment mode select means is characterized in that there is provided output pulse monitor control means for blinking said chosen indicator at a timing synchronized with the low-frequency pulses produced.

When an arbitrary treatment mode is selected by use of the treatment mode select means, one of the indcators is turned on in association with the selected treatment mode and starts blinking in synchronism with the produced low-frequency pulses. As a result, by use of an indicator, a display of a selected treatment mode and a monitoring of the output operation of pulses can be conducted, which consequently unnecessitates the indicator to indicate the output operations of pulses.

BRIEF DESCRIPTION OF THE DRAWINGS

These and other objects and advantages of the present invention will become apparent by reference to the following description and accompanying drawings wherein.

DESCRIPTION OF THE PREFERRED EMBODIMENT

Figure 1:
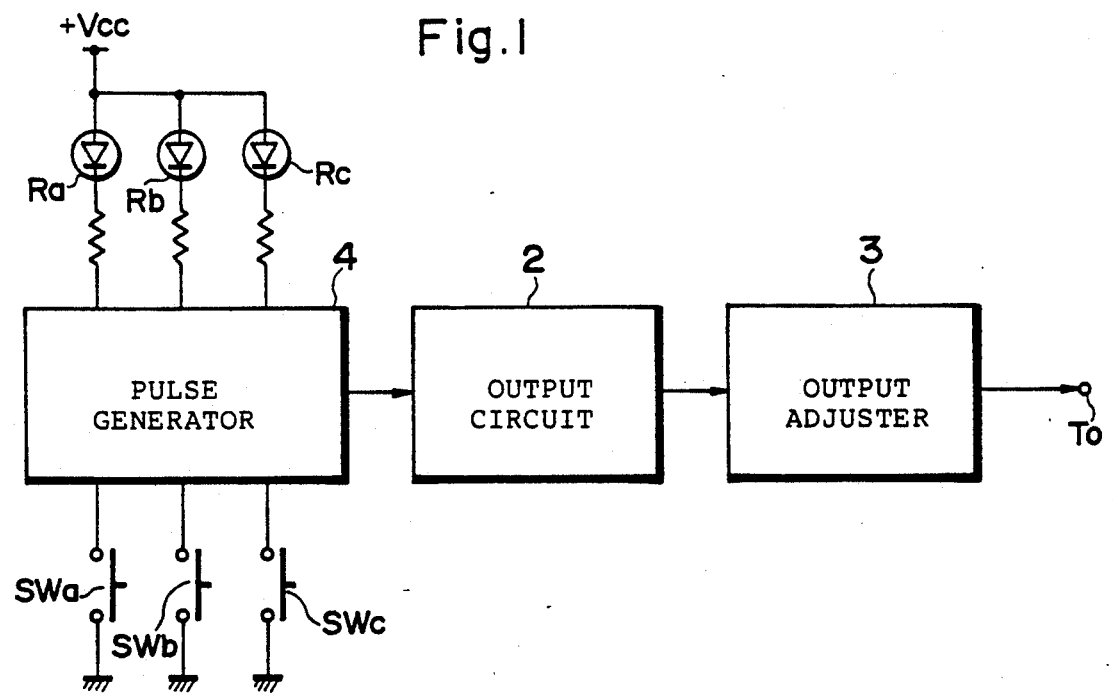
FIG. 1 is a functional block diagram showing an embodiment according to the present invention.

Referring now to the drawings, description will be given of an embodiment according to the present invention.

FIG. 1 is a functional block diagram showing an embodiment of a transcutaneous electric nerve stimulator according to the present invention. Incidentally, the portions of this configuration which are identical to those of FIG. 3 described above are labelled with the same reference numerals, and description thereof will be omitted.

Figure 3:
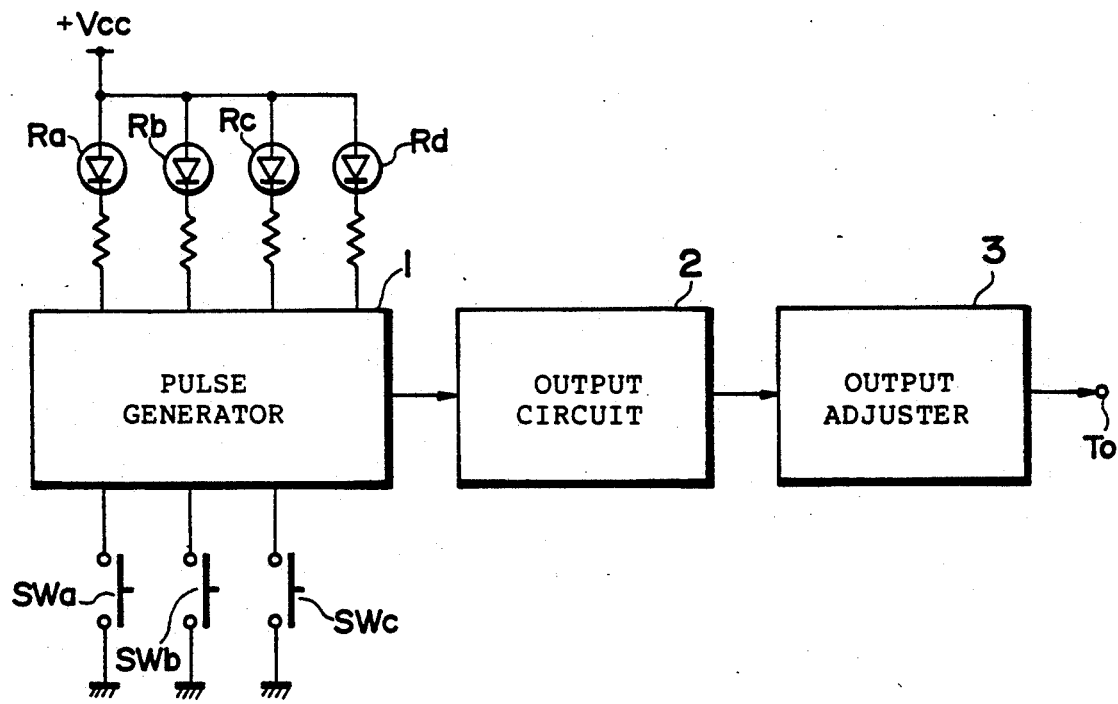
FIG. 3 is a functional block diagram showing a conventional transcutaneous electric nerve stimulator.

In the system of this diagram, reference numeral 4 indicates a pulse generator which develops, in addition to a function similar to that of the pulse generator 1 of FIG. 3 to generate pulses of a frequency corresponding to a selected treatment mode as described above, a function to blink one of the light emission diodes Ra to Rc corresponding to the selected treatment mode at a timing synchronized with the pulses produced. In other words, when a treatment mode selection switch SWa, Swb, or SWc is turned on, the light emission diode Ra, Rb, or Rc is caused to blink at a timing synchronized with pulses of 1 Hz, 10 Hz, or 50 Hz, respectively. The pulse generator 4 may also be implemented by use of a microprocessor or a combination of an oscillator and a control circuit thereof.

Figure 2:
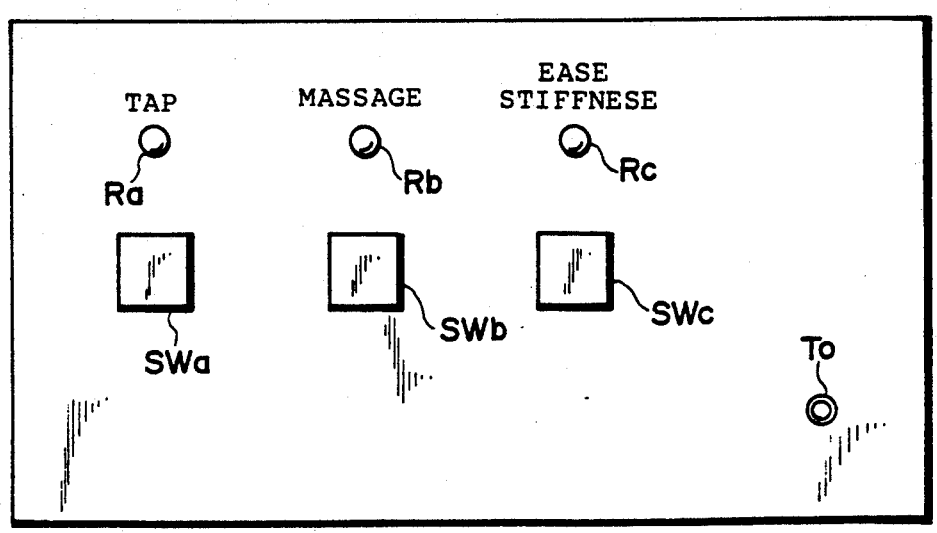
FIG. 2 is a diagram showing an appearance of a front panel of the embodiment of FIG. 1.

FIG. 2 shows the appearance of a front panel of the embodiment. As shown in this diagram, the light emitting diodes Ra to Rc are disposed on the front panel above positions where the respective treatment mode selection switches SWa to SWc are located.

As described above, since the light emitting diodes Ra to Rc displaying utilization states of the respective treatment mode selection switches SWa to SWc blink in synchronism with the produced pulses, the light emitting diode to monitor the output of the pulses becomes unnecessary.

Incidentally, although the embodiment above includes the light emitting diodes Ra to Rc, the present invention is not restricted to light emitting diodes. For example, there may also be used lamps, liquid crystal indicators, and the like.

According to the present invention, since a transcutaneous electric nerve stimulator having indicators each for indicating a treatment mode selected by use of treatment mode select means is provided with output pulse monitor control means for causing said indicator selected depending on the setting mode to blink at a timing synchronized with the low-frequency pulses produced, an indicator which is conventionally necessitated and which indicates an output operation of pulses becomes unnecessary. In consequence, the display operation can be simplified. In this case, since the power consumption of the stimulator is reduced, when the present invention is applied to a transcutaneous electric nerve stimulator to be operated with the batteries, the life of batteries can be elongated. Furthermore, since the indicator required to indicate the output operation of pulses can be dispensed with, the production cost of the apparatus can be accordingly minimized.

While the particular embodiment of the invention has been shown and described, it will be obvious to those skilled in the art tht various changes and modifications may be made without departing from the present invention in its broader aspects.

We claim:

1. A transcutaneous electric nerve stimulator comprising:
   means for selecting a treatment mode;
   a plurality of indicators respectively disposed in association with treatment modes which can be set in the stimulator;
   pulse generator means for producing a low-frequency pulse having a frequency associated with a selected treatment mode; and
   output pulse monitor control means for causing said indicator corresponding to the selected treatment mode to blink in sychronism with the produced low-frequency pulse.

2. A transcutaneous electric nerve stimulator according to claim 1 wherein:
   said means for selecting a treatment mode comprises a plurality of switches; and
   said switches and said indicators indicating a mode selected by one of said switches associated with said indicators are arranged on a panel with a predetermined correspondence therebetween.

3. A transcutaneous electric nerve stimulator according to claim 1, wherein the frequencies associated with said treatment modes are different from each other.

* * * * *